(12) United States Patent
Wagner et al.

(10) Patent No.: US 6,796,182 B2
(45) Date of Patent: Sep. 28, 2004

(54) METHOD FOR TESTING STUDS AND CORRESPONDING DEVICE

(75) Inventors: Joachim Wagner, Frechen (DE); Walter Schappacher, Bad Dürkheim (DE)

(73) Assignee: Agfa NDT GmbH (DE)

( * ) Notice: Subject to any disclaimer, the term of this patent is extended or adjusted under 35 U.S.C. 154(b) by 0 days.

(21) Appl. No.: 10/332,751

(22) PCT Filed: May 12, 2001

(86) PCT No.: PCT/DE01/01823
§ 371 (c)(1),
(2), (4) Date: Apr. 15, 2003

(87) PCT Pub. No.: WO02/06817
PCT Pub. Date: Jan. 24, 2002

(65) Prior Publication Data
US 2003/0154791 A1 Aug. 21, 2003

(30) Foreign Application Priority Data
Jul. 13, 2000 (DE) ........................ 100 34 010

(51) Int. Cl.⁷ .............................. G01N 29/20
(52) U.S. Cl. ......................... 73/588; 73/600
(58) Field of Search .................. 73/588, 596, 599, 73/600, 632

(56) References Cited
U.S. PATENT DOCUMENTS 4,588,873 A * 5/1986 Fenn et al. .................... 73/598
5,383,366 A   1/1995 Wallingford et al.
5,920,014 A   7/1999 Waschkies

FOREIGN PATENT DOCUMENTS

EP   0 833 151 A2   4/1998
FR   2 745 087 A1   8/1997

* cited by examiner

Primary Examiner—John E. Chapman
(74) Attorney, Agent, or Firm—Akerman Senterfitt

(57) ABSTRACT

A method for non-destructive testing of a weld joint of a bolt welded onto a contact area on a planar sheet metal using the lift ignition method uses directed ultrasonic signals. During the welding operation a weld pool having a modified material structure is formed beneath the contact area in the sheet metal. Ultrasonic signals are transmitted into the sheet metal using a directed and obliquely transmitting ultrasonic transmitter positioned at a coupling-in point A. An ultrasonic receiver is positioned at a coupling-out point B and receives the ultrasonic signals transmitted through the sheet metal at the coupling-out point B, an acoustic path being formed between the coupling-in point A and the coupling-out point B. The acoustic path is positioned so that it passes a center of the contact area in a distance d from this center, d being smaller than the radius of an intact weld pool and bigger than the radius of a non-intact weld pool, and the intensity of the ultrasonic signals transmitted along the acoustic path from the coupling-in point A to the coupling-out point B is detected.

15 Claims, 2 Drawing Sheets

METHOD FOR TESTING STUDS AND CORRESPONDING DEVICE

Figure 1:
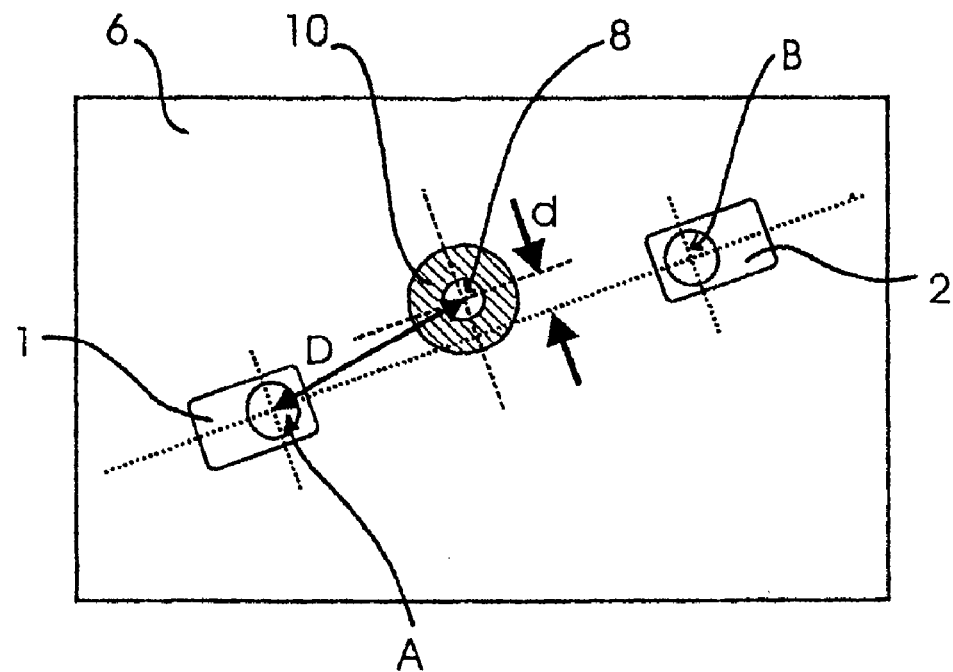

The present invention relates to a method for the non-destructive testing of welding joints between sheets of metal and bolts welded onto the same, in particular stud bolts welded on using the stroke ignition method. Such bolts having various geometrical shapes which are welded on using the fast-welding method are used in a wide variety of applications, e.g. as fastening elements for body-making in the automobile industry. Fast-welding methods are mostly automatic and are widely used in industry. Up to now, quality testing of the weld joints produced automatically is still problematic. Such tests are necessary in many cases as safety-relevant joints are often implemented using welded-on stud bolts.

Until now, the only type of testing methods implemented in practice are purely mechanical ones. These are based on determining mechanical characteristics of the weld joints to be tested, in the present case especially the tear-off, bending or turn-off momentum of the welded-on bolt. However, one of the problems in connection with the mechanical testing methods is that an earlier damage and thus a possible later fault of the weld joint tested cannot be excluded.

Known non-destructive testing methods relying on the use of ultrasonic sound are essentially based on detecting the attenuation of ultrasonic signals spreading in the direction of the longitudinal axis of the welded-on bolt during the reflection on and/or the transmission through the weld pool of the weld joint to be tested. Until now, only longitudinal waves were used in such tests. Such testing methods were implemented by means of test heads emitting sound waves in a perpendicular direction in single-head operation. Because of the generally uneven surface of the bolt head, the longitudinal waves were introduced from the rear side of the even sheet metal surface. Thus, pulse-reflection methods operating in the direction of the bolt's longitudinal axis were used.

Such testing methods based on ultrasonic sound have not yet reached a degree of reliability justifying their use for testing weld joints between bolts and sheet metal as a standard. These ultrasonic sound testing methods exhibited an unsatisfactory correlation between the results of the ultrasonic test and those of the mechanical testing methods.

This object is achieved by a method comprising the features specified in claim 1 and by an apparatus comprising the features specified in claim 10.

The basic idea of the method according to the present invention is to distinguish intact weld joints from faulty weld joints on the basis of the weld pool diameter. A weld pool represents that part of a sheet metal in which the material structure has changed due to the welding operation in comparison to the non-rolled sheet metal. Thus, the method according to the present invention is based on the detection of the weld pool diameter. The most decisive criterion is whether a minimum diameter for a predetermined weld joint has been achieved or not.

Of course, this minimum diameter of the weld pool depends upon the specific parameters of the weld joint to be tested. The factors requiring particular consideration include the geometry of the welded-on stud bolt, the geometry of the sheet metal, the material characteristics of the stud bolt and the sheet metal as well as the specific characteristics of the welding method used. With respect to a predetermined combination of stud bolt and sheet metal and a defined welding method, it is possible, for example within the framework of preliminary tests, to determine the diameter of the weld pool using the non-destructive testing method according to the present invention. Thereafter, the known mechanical testing methods may be used to determine from which diameter of the weld pool the weld joints can be regarded as intact. In this way, a standard minimum radius of the weld pool can be determined.

The testing method according to the present invention used for preferably automated testing of such weld joints, is essentially based on examining the weld joint to be tested to find out whether the standard minimum radius of the weld pool determined during the preliminary tests has been reached in the actual case or not. In this way, a secure classification of the weld joint to be tested is possible.

The method according to the present invention is based on a directed spreading of ultrasonic signals in the sheet metal onto which a stud bolt has been welded. Here, the direction of sound propagation of the ultrasonic signals comprises at least one component directed towards the extension direction of the sheet metal. Thus, the ultrasonic signals can be made to penetrate into the sheet metal at a first point A and coupled out of the sheet metal at a second point B with the points A and B being spaced apart from each other. The ultrasonic penetration is performed by an ultrasonic source sending sound signals in an oblique direction into the coupling-in point A. The ultrasonic signals are coupled out at the coupling-out point B using an ultrasonic receiver being specifically sensitive for ultrasonic signals being obliquely incident from the direction of the coupling-in point A. In particular, the ultrasonic receiver may have essentially the same ultrasonic acoustic characteristics as the ultrasonic transmitter. In general, the acoustic path extending from the coupling-In point A to the coupling-out point B tends to comprise a plurality of reflections at the surfaces of the sheet metal. Preferably, the distance between the coupling-in point A and the coupling-out point B Is chosen so that, in the light of the given material characteristics of the sheet metal and the ultrasonic parameters, the undisturbed acoustic path of the ultrasonic signals penetrating into the sheet metal at the coupling-In point A essentially hits the coupling-out point B.

For testing a weld joint using the method according to the present invention, the coupling-in point A and the coupling-out point B are placed on the sheet metal so that the connecting line between both points A and B passes at least through the edge area of the weld joint to be tested. The minimum distance of the connecting line between both points from the centre of the contact area is indicated by the reference sign d. By displacing in parallel the connecting line between A and B, it is now possible in principle for the ultrasonic signals to scan the entire weld pool of the weld joint to be tested.

The method of the present invention is based on the fact that the weld pool of the weld joint to be tested due to its modified material structure has other ultrasonic acoustic characteristics than the material structure of the sheet metal which in general has been manufactured in a rolling process. These modified ultrasonic acoustic characteristics of the weld pool cause a reduced transmission between the coupling-in point A and the coupling-out point B if the welded structure were located between these two points, i.e. if the path of the ultrasonic signals passes through the weld pool.

When the intensity of the ultrasonic signals transmitted from point A to point B is recorded location-related as a function of the distance d, it is possible to determine the size of the weld pool from the shape of the resulting graph. The location-related recording of the intensity of the ultrasonic signals can be used in particular within the framework of the preliminary tests described for determining the diameter of weld joints classified as intact. In this case, it is preferred with regard to a given weld joint to determine a standard minimum radius of the weld pool of the weld joint to be tested and to classify this weld joint to be tested as intact if said minimum radius is exceeded. Should the standard minimum radius not be reached, the respective weld joint to be tested will be classified as faulty. During the practical test, it is possible for example to use a standardised signal level on the flange of the resulting graph of ultrasonic intensity.

In a first embodiment of the method according to the present invention, which can be preferably used within the framework of automated manufacturing and testing methods, the attenuation of ultrasonic signals moving at a distance x from the centre of the weld joint to be tested from point A to point B. This minimum distance x of the acoustic path is equivalent to the minimum distance d between the connecting line A-B and the centre of the contact area indicated by the reference sign d. Here, this distance d is chosen so that the connecting line between A and B extends on or within the standard minimum radius of the weld pool which is regarded as a minimum requirement for classifying the weld joint as intact. In particular, d can be chosen exactly so that the acoustic path of the ultrasonic signals does not scan the weld pool of the weld joint to be tested if this weld pool does not reach the standard minimum radius, i.e. if the weld joint has to be classified as faulty.

Several developments can be used to further enhance the sensitivity of the method according to the present invention. A first sensitivity enhancement of the method according to the present invention is achieved when transversally polarised ultrasonic signals are used in the method according to the present invention. In contrast to the longitudinal waves used in the non-destructive ultrasonic testing methods of the prior art, transversally polarised ultrasonic waves offer a significantly enhanced sensitivity with respect to the material structure of the material in which they spread. In particular, transversally polarised ultrasonic waves undergo a significantly larger attenuation in the more coarse grained material structure of the weld pool than longitudinal waves. Thus, in an advantageous development of the method according to the present invention, mainly transversal waves are excited within the sheet metal. It was found to be especially advantageous when with regard to the ultrasonic capacity at least 75% of the ultrasonic signals generated in the sheet metal are transversally polarised. It is especially advantageous when with regard to the ultrasonic capacity more than 90% of the ultrasonic signals penetrating into the sheet metal are transversally polarised. From the viewpoint of the measuring technology, it is highly advantageous to generate a proportion as large as possible of transversally polarised ultrasonic waves in the sheet metal as this on the one hand principally enhances the sensitivity of the measuring method and on the other hand significantly simplifies the measuring technological evaluation of the ultrasonic signals received at the coupling-out point B. Therefore, any optimisation of the method according to the present invention will always aim at sending a proportion as large as possible of transversally polarised ultrasonic waves into the sheet metal.

This can be achieved advantageously by adapting the penetration angle of the ultrasonic transmitter to the material characteristics of the sheet metal and by adjusting the characteristic parameters of the ultrasonic beam transmitted such as frequency. If an appropriate penetration angle is selected, it is possible to excite only transversal waves in the sheet metal. This phenomenon has been known since long and can be studied in the relevant technological literature dealing with the basic features of ultrasonic waves. It allows in particular to achieve a complete conversion of the generally longitudinally polarised ultrasonic waves transmitted by the ultrasonic transmitter to transversally polarised ultrasonic waves in the sheet metal.

Another development of the method according to the present invention is based on the perception that in case of an intact weld joint it is possible to couple the ultrasonic signals spreading in the sheet metal from A to B into the welded-on bolt. Such coupling-in of the ultrasonic signals into the bolt results in a further attenuation of the ultrasonic signals transmitted through the weld pool, i.e. a further decrease in signal intensity at the coupling-out point B. In order to make the best use of this effect, it is necessary to adjust the acoustic path of the ultrasonic signals in the sheet metal so that the geometric acoustic path as precisely as possible hits the contact area in which the bolt has been welded onto the sheet metal. This can be accomplished by having the ultrasonic signals experience a reflection at this point of the surface of the sheet metal. If the weld joint between the sheet metal and the bolt were properly executed, a particularly high coupling-in level of the ultrasonic signals into the stud bolt is achieved.

In the so-called near field, the directed ultrasonic signals sent by the ultrasonic transmitter into the sheet metal comprise a focus point in which the acoustic pressure has a global maximum. This global maximum is connected with a minimum diameter of the directed ultrasonic beam. Thus, a particularly high location-related resolution of the method according to the present invention can be achieved when the weld pool of the weld joint to be tested is scanned essentially by the focus of the directed ultrasonic beam. Depending upon the material characteristics of the sheet metal and the properties of the ultrasonic transmitter used, in particular its vibration frequency, a focus diameter of one millimetre or less can be achieved. Thus, the diameter of the weld pool can easily be determined with comparable accuracy using the method according to the present invention if the length of the acoustic path between the coupling-in point A and the contact area of the weld joint to be tested is approximately equal to one near field length.

The apparatus according to the present invention is specifically designed so as to apply the method according to the present invention. It comprises an ultrasonic transmitter for transmitting directed ultrasonic signals into the sheet metal at a coupling-in point A and an ultrasonic receiver to couple out, at a coupling-out point B, the ultrasonic signals which were transmitted by the ultrasonic transmitter into the sheet metal and further transmitted through it. Here, the ultrasonic transmitter is designed so as to transmit the signals in an oblique direction. The ultrasonic receiver is arranged relative to the ultrasonic transmitter so that it is located on the acoustic path of the ultrasonic signals in case of an undisturbed spreading of the ultrasonic signals in the metal sheet, i.e. in the sheet metal onto which no bolt has been welded. Here, the ultrasonic receiver is sensitive to oblique incident ultrasonic signals. In particular, the ultrasonic receiver has the same ultrasonic acoustic properties as the ultrasonic transmitter. Further, a spacing device is provided which is designed so as to set a defined distance d from the connecting line between the coupling-in point A end the coupling-out point B to the centre of the contact area of the weld joint to be tested.

When the spacing device is designed so as to select a fixed distance d, said distance d is to be preferably selected shorter than the standard minimum radius of the weld pool of a weld joint to be classified as faultless. This selection of the distance d ensures that the acoustic path of the ultrasonic signals always passes through the weld pool of an intact weld joint.

Further, particular advantages are achieved when the distance d is selected to be longer than the standard radius of the weld pool of a weld joint to be classified as faulty, which radius has also been determined during the preliminary tests.

A combination of the two features last mentioned allows to implement an apparatus the ultrasonic signals of which pass through the weld pool of an intact weld joint while not contacting the weld pool of a faulty weld joint. This course of the acoustic path in the sheet metal allows a secure classification of the weld joint to be tested on the basis of the attenuation occurring between the coupling-in point A and the coupling-out point B, for example compared with undisturbed signal spreading in a sheet metal not comprising a welded-on bolt.

In another advantageous embodiment of the apparatus according to the present invention, the spacing device is designed so that the distance d may be varied. It is especially advantageous when the spacing device is designed so that the entire weld pool of the weld joint to be tested can be scanned by the ultrasonic signals, i.e. that the acoustic path of the ultrasonic signals between the coupling-in point A and the coupling-out point B can be displaced in parallel by varying the distance d so as to scan the entire weld pool.

Figure 2:
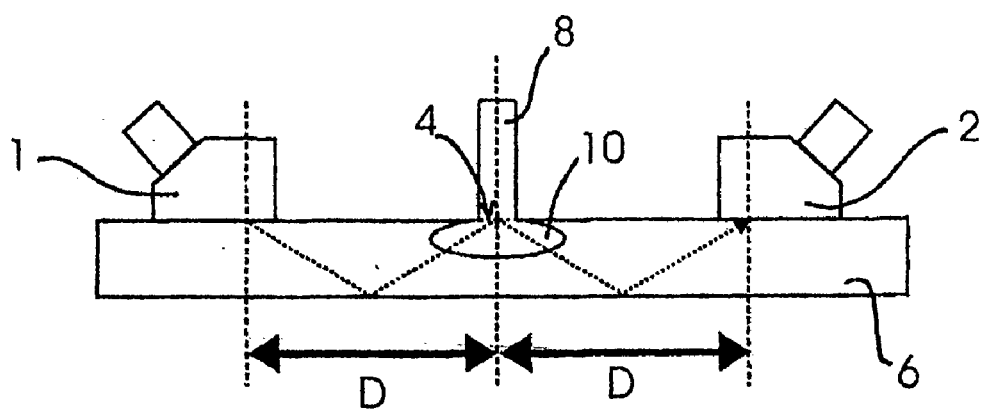
Figure 3:
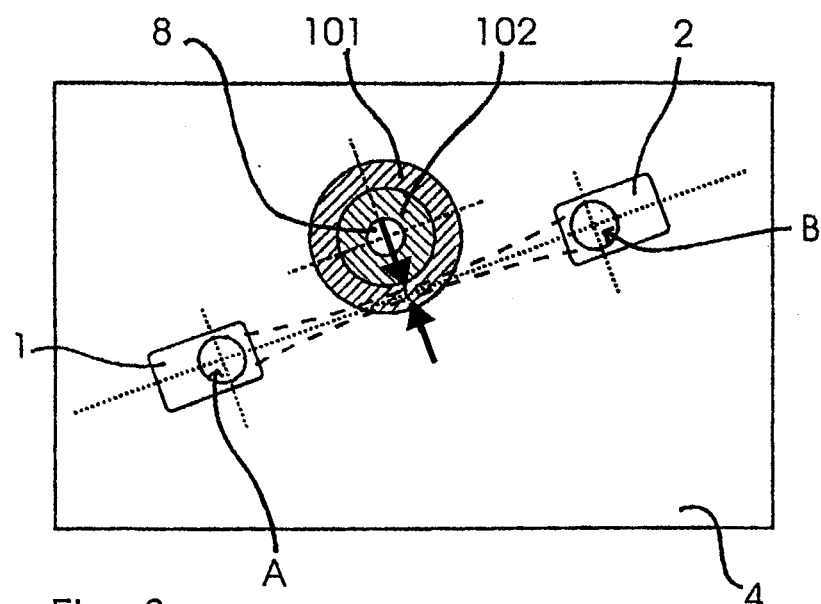
Figure 4:
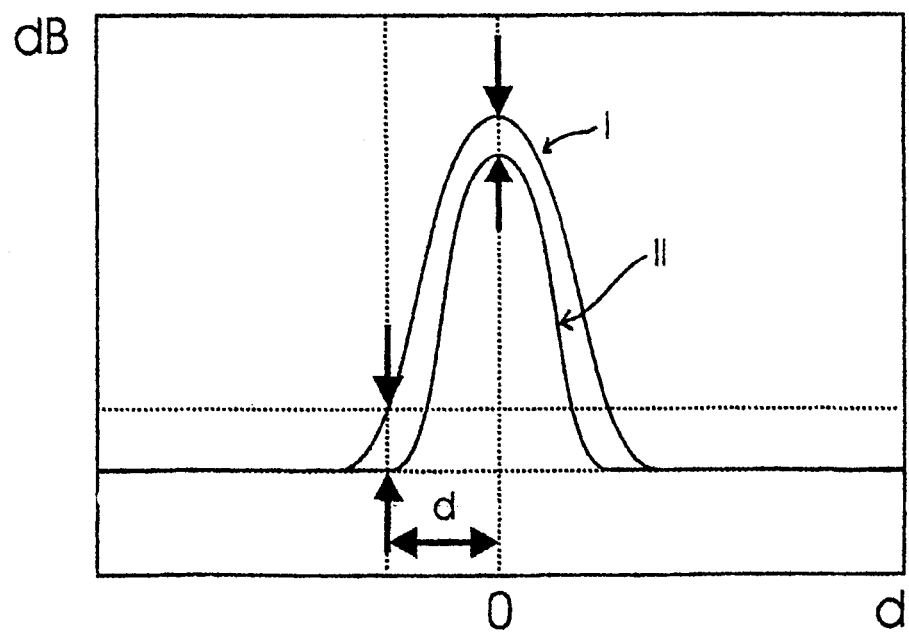

Further embodiments and advantages of the method and apparatus according to the present invention will become apparent from the following description of example embodiments which are not intended to be limiting and which are explained with reference to the drawings in which:

FIG. 1 shows a plan view of a sheet metal comprising a welded-on bolt with an ultrasonic transmitter and ultrasonic receiver being properly placed on it, FIG. 2 shows a sectional side view of the sheet metal with the welded-on bolt, wherein the sectional plane extends through the longitudinal axis of the welded-on bolt, FIG. 3 shows a plan view of a sheet metal with a welded-on bolt, wherein two different weld pool diameters are shown as examples, and FIG. 4 shows the location-related course of the attenuation of the ultrasonic signals transmitted through the sheet metal from point A to point B as a function of the distance d from the contact area.

FIG. 1 schematically shows a plan view of an arrangement which is suitable for applying the method according to the present invention. A stud bolt 8 is put on a planar sheet metal 6. The sheet metal 6 and the bolt 8 are in contact with each other on a contact area 4. The bolt 8 is welded onto the sheet metal 6 using an appropriate welding technique such as the lift ignition method. As a result, the so-called weld pool 10 is formed within the sheet metal beneath the bolt 8 with said weld pool 10 having a modified material structure. This has been schematically drawn as a plan view in FIG. 1 while it can be conceived clearer in the sectional view of FIG. 2. In general, the weld pool 10 has the shape of a drop.

For testing the weld joint between the sheet metal 6 and the bolt 8, an ultrasonic transmitter 1 is placed onto the sheet metal to transmit directed ultrasonic signals at the coupling-in point A into the sheet metal. These ultrasonic signals are directed at an angle other than zero degrees against the normal towards the sheet metal surface at the coupling-in point A. such an oblique transmission results generally in the zigzag-shaped acoustic path of the ultrasonic signals as shown in FIG. 2. The transmitted ultrasonic signals are reflected by the respective surfaces of the sheet metal 6 so that the ultrasonic signals spread longitudinally along the extension direction of the sheet metal. FIG. 2 shows that the ultrasonic transmitter 1 is arranged at such a distance D from the contact area 4 that the contact area 4 or at least the weld pool 10 of a weld joint to be classified as intact is located on the acoustic path. For a given transmission angle into the sheet metal, the distance D has to be selected so as to be properly adapted. At the same time, the direction of the ultrasonic signals transmitted into the sheet metal by the ultrasonic transmitter 1 has to be selected so as to be properly adapted.

The ultrasonic signals transmitted into the sheet metal 6 by the ultrasonic transmitter 1 at the coupling-in point A pass through the contact area 4 and/or the weld pool 10 where they undergo a more or less strong attenuation, and further spread in the sheet metal 6. For coupling out these ultrasonic signals being transmitted through the weld pool 10, an ultrasonic receiver 2 is arranged at the coupling-out point B. The coupling-out point B is selected so as to be positioned on the acoustic path of the undisturbed ultrasonic signals in the sheet metal 6.

As an ultrasonic receiver 2, an ultrasonic receiver is used which is sensitive to ultrasonic signals being incident at the coupling-out point B at an angle other than zero degrees against the surface normal. In particular, the ultrasonic transmitter 1 and the ultrasonic receiver 2 may have essentially equal ultrasonic acoustic properties.

The plan view of FIG. 1 shows that the acoustic path indicated by the straight line through the points A and B passes along the centre of the contact area 4, i.e. the longitudinal axis of the bolt 8. Depending upon the selected distance d of the straight line across A and B from the centre of the contact area 4, the weld pool of the weld joint to be tested is penetrated by the ultrasonic signals or not. Depending upon the condition of the weld joint to be tested and the position at which the weld pool of the weld joint to be tested is penetrated, a varying attenuation of the ultrasonic signals transmitted from point A to point B occurs. Thus, the attenuation occurring with a given distance d can be used as a measure for assessing the spatial dimension of the weld pool and thus the quality of the weld joint.

If the ultrasonic transmitter 1 and the ultrasonic receiver 2 are continuously displaced across the weld pool 10 of the weld joint to be tested, the transmitted intensity or, as an equivalent, the attenuation of the transmitted ultrasonic signals is obtained as a function of the distance d. Such a location-related signal course is shown in FIG. 4. Here, the measured attenuation of the transmitted ultrasonic signals, compared with undisturbed signal spreading in a sheet metal not comprising a welded-on bolt 8, is laid off as ordinate while the distance d of the straight connecting line between A and B from the centre of the contact area 4 is laid off as abscissa. The upper graph indicated by the reference sign I shows the signal course through a weld joint to be classified as intact, the weld pool 101 of which has a large diameter. With regard to large values of d, it can be seen that no additional attenuation occurs relative to the undisturbed signal spreading in the sheet metal 6. As soon as the weld pool 10 of the weld joint to be tested comes in the way of the acoustic path, an attenuation of the transmitted ultrasonic signals begins to occur and increases continuously up to the centre of the weld pool 10 followed by an essentially symmetric drop of the signal.

A weld pool diameter can be directly read from the shape of the graph. It is possible to define as this diameter, for example, that diameter at which the transmitted signals have dropped by, for example, three decibel compared with the undisturbed signals. In this manner, the weld pool diameters of weld joints can be determined during preliminary tests, which weld joints are then tested for their durability by conventional mechanical testing methods. It is thus possible to determine a weld pool diameter or, as an equivalent, a weld pool radius which is required as a minimum to allow the classification of the weld joint to be tested as intact. During preliminary tests, a larger number of weld joints are tested to determine from the results a standard minimum weld pool radius from which on a weld joint can be classified as intact.

Graph II in FIG. 4 illustrates the signal course during a test of a weld joint to be classified as faulty the weld pool 102 of which has a reduced diameter. This becomes fully obvious by comparing the graphs I and II.

This effect can advantageously be used to distinguish between intact and faulty weld joints on the basis of a single transmission measurement. It is advantageous to select the distance d of the connecting line between A and B so that the acoustic path of the ultrasonic signals is just out of contact with the weld pool of a weld joint to be classified as faulty while passing through the edge portion of a weld pool of a weld joint to be classified as intact. Accordingly, the distance d is selected to be slightly shorter than the standard minimum radius of the weld pool 10 of a weld joint to be classified as intact.

On the other hand, the weld pool 10 of a weld joint to be classified as faulty has a smaller radius so that it is not scanned by the ultrasonic signals. So, if a weld joint having an unknown weld pool radius is tested in this manner, a faulty weld joint would result in a reduced or missing attenuation of the ultrasonic signals transmitted from point A to point B. In case of an intact weld joint, however, the ultrasonic signals pass through the edge area of the weld pool 10 of the weld joint where they are attenuated. Thus, an attenuation of the ultrasonic signals transmitted from point A to point B will occur.

In accordance with the approach to determining the weld pool diameter during preliminary tests, a threshold is defined to specify from which minimum attenuation of the ultrasonic signals transmitted from point A to point B the weld pool 10 of the weld joint to be tested has a diameter of sufficient size so as to be classified as intact.

It is especially advantageous to apply the method according to the present invention if a device is used which fixes the ultrasonic transmitter 1 and the ultrasonic receiver 2 relative to each other. In this case, it is advantageous to select the distance D between the ultrasonic transmitter 1 and the centre of the contact area 4 or the weld pool 10 of the weld joint to be tested so as to be scanned by the ultrasonic signals. The distance d between the connecting line between A and B is fixedly set by a spacing device which for example may be implemented as an inserting sleeve comprising a bore hole. A defined displacement by the distance d may for example be implemented by providing an eccentric design of the bore hole.

Further, particular advantages for implementing the method become apparent when the ultrasonic transmitter 1 is arranged at such a distance D from the weld joint to be tested that the directed ultrasonic signals comprise an acoustic pressure centre at the minimum distance d of the A-B connecting line from the centre of the weld joint. This may for example be implemented by positioning the ultrasonic transmitter 1 spaced apart from the point of the minimum distance d by approximately one near field length.

If the ultrasonic receiver 2 comprises essentially the same ultrasonic acoustic properties as the ultrasonic transmitter 1, the ultrasonic receiver 2 is positioned symmetrically to the centre of the weld joint at the same distance D from the latter. Thus, the distance between the ultrasonic transmitter 1 and the ultrasonic receiver 2 essentially amounts to two near field lengths. A particularly high resolution can be achieved by scanning the weld pool 10 with the focus of the directed ultrasonic signals.

If, as shown in FIG. 2, the ultrasonic transmitter 1 is arranged so that the contact area 4 or at least the weld pool 10 of the weld joint to be tested is located on the acoustic path of the ultrasonic signals, an intact weld joint will result in an enhanced coupling-in of the ultrasonic signals into the welded-on bolt 8. This causes a reduced transmission of the ultrasonic signals from point A to point B. The coupling-in into the bolt 8 is particularly strong in case of transversally polarised ultrasonic waves. This effect is also apparent in FIG. 4. One clearly sees a different shape of the graph in the centre of the weld joint to be tested depending upon whether the weld joint to be tested is to be regarded as intact or faulty. Graph I illustrates the shape denoting an intact weld joint by presenting a stronger maximum attenuation than graph 11 which illustrates a faulty weld joint. Furthermore, this effect causes a distinctly different transmission or attenuation of the ultrasonic signals depending upon whether they pass through the weld pool 10 of an intact or faulty weld joint.

Finally, it has become clear evident that a particularly high sensitivity of the method according to the present invention can be achieved when essentially only transversally polarised ultrasonic waves are used. These transversally polarised ultrasonic waves show a stronger attenuation during their passage through the coarser-grained structure of the weld pool than the longitudinally polarised ultrasonic signals used hitherto. Thus, the use of transversally polarised ultrasonic waves can further enhance the sensitivity of the method according to the present invention. In this case, the ultrasonic transmitter 1 of FIG. 2 is advantageously optimised so as to transmit essentially only transversally polarised ultrasonic waves into the sheet metal 6. By employing the fraction laws for ultrasonic waves at the transition between media having different acoustic velocities, this can be performed so that practically the entire intensity transmitted is converted into transversally polarised ultrasonic waves in the sheet metal 6. The use of completely transversally polarised ultrasonic waves as far as possible in the sheet metal 6 is especially advantageous in the method according to the present invention, on the one hand due to the aforementioned higher sensitivity to structure modifications and on the other hand due to the signal detection and processing being significantly simpler from a technical measurement point of view as only one polarisation type of ultrasonic waves has to be detected. If a mixture of longitudinally and transversally polarised ultrasonic waves is used, a superposition of two signals being attenuated to a different degree has to be resolved resulting in additional technical measurement efforts.

The ultrasonic signals recorded by the ultrasonic receiver 2 are transmitted to a signal processing device not shown in the figures. Such device may for example be capable of detecting and evaluating a signal course analogous to FIG. 4. It may as well be designed in a simpler way in which the ultrasonic signal actually detected is compared with a previously stored standard value. Such a standard value may for example be related to the undisturbed ultrasonic spreading in the sheet metal 6 without a welded-on bolt 8. Further, such a standard value may of course be related to the ultrasonic spreading in the sheet metal 6 including a bolt 8 provided that the weld joint of which is faulty. Any other standard values are conceivable and can be implemented.

In the example embodiment shown, the method according to the present invention is designed for being applied with volume waves spreading in the sheet metal by multiple reflection on the surfaces of the sheet metal. However, the method according to the present invention is not basically limited thereto; the use of surface waves spreading on the sheet metal surface is conceivable and possible as well.

What is claimed is:

1. A method for non-destructive testing of a weld joint of a bolt welded onto a contact area on a planar sheet metal using the stroke ignition method, whereby during the welding operation a weld pool having a modified material structure is formed beneath the contact area in the sheet metal, the method using directed ultrasonic signals and comprising the following steps:

a) transmitting of ultrasonic signals into the sheet metal using a directed and obliquely transmitting ultrasonic transmitter positioned at a coupling-in point A located on the planar sheet;

b) positioning an ultrasonic receiver at a coupling-out point B located on the planar sheet and receiving the ultrasonic signals transmitted through the sheet metal at the coupling-out point B, an acoustic path being formed between the coupling-in point A and the coupling-out point B; and c) positioning the acoustic path in the sheet metal between the coupling-in point A and the coupling-out point B so that the acoustic path passes a center of the contact area in a distance d from this center, d being smaller than the radius of an intact weld pool and bigger than the radius of a non-Intact weld pool, and d) detecting the intensity of the ultrasonic signals transmitted along the acoustic path from the coupling-in point A to the coupling-out point B.

2. The method according to claim 1, wherein the detected intensity of the transmitted ultrasonic signals is compared with a predetermined standard value of the intensity.

3. The method according to claim 1, wherein the distance between the contact area and the coupling-in point A equals the distance between the contact area and the coupling-Out point B.

4. The method according to claim 1, wherein essentially only transversal waves are transmitted into the sheet metal.

5. The method according to claim 1, wherein essentially only bulk waves are transmitted into the sheet metal, which volume waves spread in the sheet metal by multiple reflections on surfaces of the sheet metal.

6. The method according to claim 1, wherein the ultrasonic transmitter has a focus and wherein the ultrasonic transmitter is positioned at such a distance D from the contact area of the weld joint to be tested that the focus of the directed ultrasonic signals is formed at the contact area.

7. The method according to claim 1, wherein the acoustic path of the ultrasonic signals is selected so that a weld joint to be classified as intact results in an enhanced coupling-in of the ultrasonic signals into the bolt.

8. The method according to claim 1, wherein the intensity of the ultrasonic signals between the coupling-in point A end the coupling-out point B is detected in a location-related manner by varying the distance d of the connecting line between the coupling-in point A and the coupling-out point B from the contact area.

9. The method according to claim 1, wherein the bolt is a stud bolt.

10. The method according to claim 1, wherein the ultrasonic transmitter has a near field length end wherein the length of the acoustic path from the ultrasonic transmitter to the contact area essentially equals the near field length.

11. The method according to claim 1, wherein the distance d is varied during testing and the weld joint to be tested is scanned by the ultrasonic signals.

12. An apparatus for non-destructive testing of a weld joint of a bolt welded onto a contact area of a planar sheet metal, the bolt being welded using the stroke ignition method, and during the welding operation a weld pool having a modified material structure being formed beneath the contact area in the sheet metal, the apparatus using directed ultrasonic signals and comprising the following components a) an ultrasonic transmitter for transmitting ultrasonic signals into the shoot metal at a coupling-in point A, the ultrasonic transmitter being an angle probe obliquely transmitting directed ultrasonic signals Into the planar sheet metal, b) an ultrasonic receiver for receiving the ultrasonic signals transmitted through the sheet motel at a coupling-out point B, the ultrasonic receiver being an angle probe which angle probe is sensitive to obliquely incident ultrasonic signals, an acoustic path being formed between the coupling-in point A and the coupling-out point B, and c) a spacing device which spacing device is designed so as to set a defined distance d of a geometric connecting line between the coupling-in point A and the coupling-out point B from a center of the contact area of the weld joint to be tested.

13. The apparatus according to claim 12, wherein the distance d is selected so as to be shorter than the standard minimum radius of the weld pool of a weld joint to be classified as faultless.

14. The apparatus according to claim 12, wherein the distance d is selected so as to be longer than the standard minimum radius of the weld pool of a weld joint to be classified as faulty.

15. The apparatus according to claim 12, wherein the spacing device is arranged for varying the distance d and the weld pool of the weld joint to be tested is able to be scanned by the ultrasonic signals.

* * * * *